United States Patent [19]  
Kamiyama et al.

[11]  4,152,297  
[45]  May 1, 1979

[54] PRETREATING PROCESS FOR THE STABILIZATION OF A CATALYST FOR THE CONVERSION OF AROMATIC HYDROCARBONS

[75] Inventors: Setsuo Kamiyama, Ooi; Yukio Nagashima, Wako; Hiroshi Furukawa, Ooi; Katsumi Kaneko, both of Ooi, all of Japan

[73] Assignee: Toa Nenryo Kogyo Kabushiki Kaisha, Tokyo, Japan

[21] Appl. No.: 867,165

[22] Filed: Jan. 5, 1978

[30] Foreign Application Priority Data

Feb. 24, 1977 [JP]  Japan ................................. 52/18658

[51] Int. Cl.$^2$ ............................................. B01J 29/06
[52] U.S. Cl. .................................................. 252/455 Z
[58] Field of Search ................ 252/455 Z; 260/668 A

[56]  References Cited

U.S. PATENT DOCUMENTS

| 3,792,100 | 2/1974 | Sonoda et al. | 260/668 A |
| 3,873,632 | 3/1975 | Pollitzer | 260/668 A |
| 3,907,914 | 9/1975 | Willis et al. | 260/668 A |

Primary Examiner—Carl Dees  
Attorney, Agent, or Firm—Rebecca Yablonsky

[57]  ABSTRACT

A method of stabilizing a catalyst for the conversion of aromatic hydrocarbons in the presence of hydrogen such as the isomerization of $C_8$ aromatic hydrocarbons to increase the content of p-xylene, is carried out by contacting a catalyst in advance of start-up with hydrocarbons in the liquid phase at a temperature preferably of about 50° to about 250° C. and preferably at elevated pressure up to about 50 Kg/cm$^2$ in the absence of hydrogen; the catalyst being prepared by the acid leaching of a hydrogen form mordenite to produce a mordenite having a silica to alumina molar ratio of about 15 to 21. Preferably, the hydrocarbons used for the contacting have the composition of the feed to be converted.

11 Claims, No Drawings

PRETREATING PROCESS FOR THE STABILIZATION OF A CATALYST FOR THE CONVERSION OF AROMATIC HYDROCARBONS

BACKGROUND OF THE INVENTION

1. Field of the Invention

This invention relates to a method of preventing catalyst deactivation in the conversion of aromatic hydrocarbons particularly in a hydrogen atmosphere, by contacting the catalyst with hydrocarbons under controlled conditions in advance of start-up.

2. Description of the Prior Art

Silica-aluminas or zeolites have been utilized widely for alkylation, dealkylation, disproportionation and isomerization of aromatic hydrocarbons. However, these catalysts for the conversion of aromatic hydrocarbons have the disadvantage that their activity gradually declines due to the deposition of carbonaceous material and resulting clogging of the pore structure, especially in zeolite that has strong acid sites and small pore structure.

In order to overcome this disadvantage, methods have been proposed for preventing catalyst deactivation by partially poisoning a zeolite catalyst with a metal, by sulfiding a zeolite catalyst and, further, continuously introducing a sulfur compound into the reaction system. It has also been suggested to effect the reaction at a low temperature for the purpose of preventing deposition of carbon but the object of effecting simultaneously both the reactions of disproportionation of ethylbenzene and isomerization of xylene, for example, cannot be accomplished since the disproportionation of ethylbenzene takes place preferentially over the isomerization of xylene.

Various patent publications disclose processes wherein aromatic hydrocarbons, in some cases in the absence of hydrogen, are passed in the liquid phase over catalysts. However, such processes are not for the pretreatment of the catalysts but are for the conversion of the aromatic hydrocarbons by the reactions mentioned above. They do not employ the particular catalyst of this invention.

In U.S. Pat. No. 3,377,400, issued on Apr. 9, 1968 to J. J. Wise (assigned to Mobil Oil Corporation) a method is disclosed for subjecting alkyl aromatic hydrocarbons to isomerization or disproportionation by contact with a crystalline aluminosilicate, in the liquid phase, at temperatures below 600° F.

In U.S. Pat. No. 3,578,723 issued on May 11, 1971 to Bowes and Wise (assigned to Mobil Oil Corporation) crystalline zeolites identified as ZSM-4 are contacted with alkyl aromatics at a temperature in the range of 250° F. to 1000° F. at a pressure of up to 2000 psig at a liquid hour space velocity of 0.05 to 40 to effect rearrangements including disproportionation and isomerization.

In U.S. Pat. No. 3,856,873 issued on Dec. 24, 1974 to G. T. Burress (assigned to Mobil Oil Corporation) certain acid zeolites are brought into contact with $C_8$ aromatics to isomerize xylenes and convert at least part of the ethyl benzene to other aromatics, in the vapor phase, in the absence of added hydrogen, at a temperature of 500° to 1000° F.

On the contrary, the object of the present invention is to effect a pretreatment of a catalyst whereby its stability will be improved when it is subsequently used in the conversion of $C_8$ aromatic hydrocarbons.

SUMMARY OF THE INVENTION

The gist of the present invention consists in a method of preventing the deactivation of a catalyst in the conversion of aromatic hydrocarbons in a hydrogen atmosphere, by contacting the catalyst with hydrocarbons under selected conditions in advance of start-up. Then the conversion of an aromatic hydrocarbon feed is started with the treated catalyst which exhibits improved stability.

In our co-pending application, Ser. No. 797,992 filed May 18, 1977 incorporated herein by reference, a process is described which comprises contacting a mixture of $C_8$ aromatic hydrocarbons containing m-xylene and usually also ethylbenzene with an acid leached hydrogen form of mordenite having a silica to alumina molar ratio of 15-21 in the presence of hydrogen at a temperature of 180° to 250° C. under a pressure of atmospheric to 200 Kg/cm$^2$ and recovering a product containing an increased proportion of p-xylene. The present invention contemplates extending the life of said catalyst by preconditioning it. This invention is preferably used in combination with said conversion process and it may also be used with other hydrocarbon conversion processes.

Accordingly a method of suppressing the deactivation of a catalyst for the conversion of aromatic hydrocarbons and thereby prolonging catalyst life is provided, the catalyst being a natural or synthetic hydrogen form mordenite in which the silica to alumina molar ratio has been increased by acid leaching of the alumina, particularly to 15-21, by contacting the catalyst with hydrocarbons in a liquid phase at a temperature in the range of about 20° C. to about 270° C. and a pressure in the range of atmospheric to 50 Kg/cm$^2$ for a period of time of about 1 to 50 hours and preferably a liquid hour space velocity of 1 to 5 hr.$^{-1}$, in the absence of added hydrogen, prior to use in a conversion process of aromatic hydrocarbons.

DETAILED DESCRIPTION OF THE INVENTION

The conversion of aromatic hydrocarbons in a hydrogen atmosphere may involve any of the following: the disproportionation of alkylbenzenes such as toluene, xylene and ethylbenzene to produce benzene, toluene, xylene and diethylbenzenes; the isomerization of polyalkylbenzenes such as xylene, trimethylbenzene, tetramethylbenzene and diethylbenzene; and the hydrodealkylation of polyalkylbenzenes. In particular, the conversion may be a simultaneous disproportionation and isomerization of $C_8$ aromatic hydrocarbons. The $C_8$ aromatic hydrocarbons used as a starting material include, for example, o-xylene, m-xylene, p-xylene and ethylbenzene which are not in a thermodynamic composition and usually contain 5% by weight or more of ethylbenzene. The quantity of ethylbenzene in the starting material is preferably 40% by weight or less since, if greater than 40% by weight, the isomerization, conversion and recovery of xylenes are decreased.

The hydrocarbon used in the present invention for the contact with the catalyst in advance of start-up includes preferably aromatic hydrocarbons, in particular, $C_6$ to $C_9$, more preferably $C_6$ to $C_8$, aromatic hydrocarbons and mixtures of hydrocarbons containing aromatic hydrocarbons. In the case of a catalyst used for the conversion of $C_8$ aromatic hydrocarbons, a mixture of aromatic hydrocarbons used as a starting material for the conversion can be used at it is.

Contact of the catalyst for the conversion of aromatic hydrocarbons with a hydrocarbon is preferably carried out with heating. The temperature of contacting is ordinarily normal temperature (20° C.) to about 270° C., preferably about 50° to about 250° C. The pressure is generally set in a range such that a liquid phase can be maintained at the selected temperature and preferably ranges from normal (atmospheric) pressure to 50 Kg/cm². In particular, the contacting is preferably carried out under pressure. The contact time is ordinarily 1 to 50 hours at a liquid hour space velocity (LHSV) of 1 to 5 hr$^{-1}$, preferably 3 to 20 hours at a LHSV of 2 to 3 hr$^{-1}$.

As is apparent from the foregoing, the present invention provides an effective stabilization method for an aromatic hydrocarbon conversion catalyst without any troublesome modifications. Thereby effective simultaneous disproportionation of ethylbenzene and isomerization of xylenes with good catalyst activity maintenance for long periods of time, independently of whether gaseous or liquid phase reactions are carried out, can be achieved. The method of the present invention has another advantage in that, when a starting material for the conversion reaction is used as the hydrocarbon for the contact with the catalyst, the conversion reaction can be started directly merely by changing the conditions at the end of the contacting treatment. Furthermore, the method of the present invention is available for the catalyst carrying a metal, for example, a Group VIII metal.

The following examples illustrate the present invention.

EXAMPLE 1

A hydrogen form synthetic mordenite having a silica/alumina molar ratio of 12.5 (commercial name Zeolon 200H, manufactured by Norton Co.) was treated with concentrated hydrochloric acid to leach a part of the alumina in the mordenite, washed with water until no chlorine could be detected, dried at 100° C. for 2 hours or more and calcined at 500° C. in air for 6 hours to produce a catalyst having a silica to alumina molar ratio of 20.0. The resulting catalyst was charged to a cylindrical reactor and, in advance of start-up for the conversion reaction of aromatic hydrocarbons, it was contacted with a starting material consisting of ethylbenzene/m-xylene (23/77 by weight) under the conditions shown in Table I (Run Nos. 2 to 6). The above described hydrogen form synthetic mordenite catalyst which had not been acid treated was similarly subjected to the conditions shown (Run No. 8).

Then the starting material was continuously fed to the cylindrical reactor and the reactions were continuously carried out in vapor phase at a reaction temperature of 225° C., LHSV of 1 hr$^{-1}$ and reaction pressure of 50 Kg/cm² in the presence of hydrogen in a proportion of 2.9 mols to 1 mol of the starting hydrocarbon. In comparison, the same reaction was carried out using a catalyst which had not been pretreated by contact with the starting hydrocarbon (Run Nos. 1 and 7). Furthermore, for comparison, the same reaction was carried out using a catalyst which had been contacted with the starting hydrocarbon while supplying hydrogen in a proportion of 133.6 Nm³ per 1 Kl of the starting material (Run No. 9).

Data in Table I show the results of product analyses with the passage of time.

TABLE I

| Run No. | Contact Conditions of Catalysts | | | | Reaction Time (hr) | Ethylbenzene Conversion (%) | Xylenes Isomerization (%)* | Xylenes Recovery (%)** |
|---|---|---|---|---|---|---|---|---|
| | Temp (° C.) | Pressure (kg/cm²) | LHSV (hr$^{-1}$) | Time (hr) | | | | |
| 1 | — | — | — | — | 4 | 41 | 84 | 91 |
| | | | | | 50 | 1 | 1 | 99 |
| 2 | 50 | 50 | 2 | 3 | 4 | 47 | 94 | 88 |
| | | | | | 50 | 30 | 89 | 95 |
| 3 | 110 | 50 | 2 | 3 | 4 | 47 | 97 | 88 |
| | | | | | 50 | 40 | 96 | 92 |
| 4 | 225 | 50 | 2 | 3 | 4 | 47 | 99 | 89 |
| | | | | | 50 | 45 | 98 | 90 |
| 5 | 250 | 50 | 2 | 3 | 4 | 44 | 98 | 91 |
| | | | | | 50 | 39 | 97 | 94 |
| 6 | 300 | 50 | 2 | 3 | 4 | 6 | 69 | 99 |
| | | | | | 50 | 3 | 67 | 99 |
| 7 | — | — | — | — | 4 | 12 | 44 | 97 |
| | | | | | 10 | 3 | 12 | 99 |
| 8 | 225 | 50 | 2 | 3 | 4 | 15 | 62 | 97 |
| | | | | | 10 | 13 | 58 | 97 |
| 9 | 225 | 50 | 2 | 3 | 4 | 44 | 95 | 90 |
| | | | | | 50 | 33 | 91 | 94 |

Notes:
(These Definitions are applicable to Tables I-III)
*% Approach to an Equilibrium Concentration of p-xylene (0.241) in Three Xylene Isomers
**Recovery of Three Xylene Isomers

EXAMPLE 2

The hydrogen form synthetic mordenite catalyst acid-treated as in Example 1 was charged to a cylindrical reactor and brought into contact with a starting material consisting of toluene/ethylbenzene/p-xylene/m-xylene/o-xylene (0.8/27.5/9.5/55.4/6.8 by molar ratio) at a temperature of 225° C., LHSV of 2 hr$^{-1}$ and pressure of 50 Kg/cm² for 10 hours. Then the said starting material was continuously fed thereto and a liquid phase reaction was thus carried out at a reaction temperature of 210° C., LHSV of 1 hr$^{-1}$ and reaction pressure of 20 Kg/cm² in the presence of hydrogen in a proportion of 0.9 mol to 1 mol of the starting hydrocarbon (Run No. 10).

In comparison, the same reaction was also carried out with the catalyst that has not been contacted with the starting material (Run No. 11).

Data in Table II show the results of analyses of the product stream with increasing periods of time.

TABLE II

| Run No. | Reaction Time (hr.) | Ethylbenzene Conversion (%) | Xylenes Isomerization (%) | Xylenes Recovery (%) |
| --- | --- | --- | --- | --- |
|    | 10  | 22 | 99 | 96 |
|    | 100 | 21 | 99 | 97 |
| 10 | 200 | 22 | 98 | 97 |
|    | 300 | 23 | 98 | 96 |
|    | 400 | 22 | 99 | 97 |
|    | 4   | 20 | 66 | 97 |
| 11 | 10  | 13 | 46 | 98 |
|    | 20  | 5  | 22 | 99 |

EXAMPLE 3

Using the hydrogen form synthetic mordenite catalyst acid treated as in Example 1, the procedure of Example 1 was repeated with the exceptions that the contact with the starting material was carried out under the conditions shown in Table III and a gaseous phase reaction was carried out at a reaction temperature of 200° C. and normal pressure (Run Nos. 13 and 14).

In comparison a similar reaction was also carried out with the catalyst that had not been contacted with the starting material (Run No. 12).

Data in Table III show the results of product analyses after various times onstream.

TABLE III

| Run No. | Contact Conditions of Catalyst | | | | Reaction Time (hr) | Ethylbenzene Conversion (%) | Xylenes Isomerization (%) | Xylenes Recovery (%) |
| --- | --- | --- | --- | --- | --- | --- | --- | --- |
|    | Temp (° C.) | Pressure (Kg/cm$^2$) | LHSV (hr$^{-1}$) | Time (hr) |    |    |    |    |
| 12 | — | — | — | — | 4  | 40 | 56 | 92 |
|    |   |   |   |   | 10 | 21 | 30 | 97 |
| 13 | 110 | Normal Pressure | 2 | 3 | 4  | 43 | 65 | 91 |
|    |     |                 |   |   | 10 | 33 | 51 | 94 |
| 14 | 225 | 50 | 2 | 3 | 4  | 45 | 75 | 90 |
|    |     |    |   |   | 10 | 37 | 66 | 93 |

As is apparent from these examples, the method of the present invention has the advantage that, independently of the reaction phase and pressure, the catalyst deactivation in the disproportionation of ethylbenzene and the isomerization of xylene can effectively be prevented and the isomerization to p-xylene can be increased. In addition, it will be seen that the catalyst deactivation is not so suppressed when the contact with a starting material is carried out in the presence of hydrogen.

What is claimed is:

1. A method of pretreatment of a catalyst to be used in the conversion of aromatic hydrocarbons in a hydrogen atmosphere, being an acid leached hydrogen form mordenite having a silica to alumina molar ratio of 15 to 21, which comprises contacting the catalyst with hydrocarbons in a liquid phase at a temperature in the range of about 20° C. to about 270° C. at a pressure in the range of atmospheric to about 50 Kg/cm$^2$ for a period of time of about 1 to 50 hours in the absence of hydrogen, thereby obtaining a catalyst of improved stability.

2. A method according to claim 1 in which the liquid hour space velocity is 1 to 5 hr.$^{-1}$.

3. A method according to claim 1 in which the conversion process is applied to C$_8$ aromatic hydrocarbons and comprises the isomerization of xylenes.

4. A method according to claim 1 in which the temperature is in the range of 50° to 250° C.

5. A method according to claim 4 in which the period of time of contacting is from 3 to 20 hours and the liquid hour space velocity is from 2 to 3 hr.$^{-1}$.

6. A method according to claim 1 in which the hydrocarbons used for the contacting are aromatics.

7. A method according to claim 6 in which said hydrocarbons are C$_6$ to C$_9$ aromatics.

8. A method according to claim 1 in which the hydrocarbons used for the contacting have the composition of the feed mixture to the conversion process.

9. A method for the preconditioning of a catalyst according to claim 1 to be used in the isomerization of C$_8$ aromatic hydrocarbons which comprises contacting the catalyst with hydrocarbons having the composition of the feed to the isomerization and containing xylenes and ethylbenzene, in the absence of hydrogen, in the liquid phase, at a temperature in the range of 50° to 250° C. and a pressure in the range of atmospheric to about 50 Kg/cm$^2$ for a period of time of 3 to 20 hours at a liquid hour space velocity of 1 to 5 hr.$^{-1}$ thereby obtaining a catalyst of improved stability.

10. In a method for the conversion of C$_8$ aromatic hydrocarbons wherein xylenes are isomerized which comprises contacting a mixture of C$_8$ aromatic hydrocarbons containing m-xylene and ethylbenzene with an acid leached hydrogen form mordenite catalyst having a silica to alumina molar ratio of 15-21 in the presence of hydrogen at a temperature of 180° to 250° C. under a pressure of atmospheric to 200 Kg/cm$^2$, the improvement which comprises preconditioning the catalyst by contacting it with aromatic hydrocarbons at a temperature in the range of about 50° C. to about 250° C. at a pressure in the range of atmospheric to 50 Kg/cm$^2$ for a period of time of about 1 to 50 hours and a liquid hour space velocity of 1 to 5 hr.$^{-1}$ in the absence of added hydrogen, thereby obtaining a catalyst of improved stability.

11. The improvement according to claim 10 in which the aromatic hydrocarbons used for preconditioning the catalyst have the composition of the feed to the conversion.

* * * * *